United States Patent
Yoon et al.

(10) Patent No.: US 10,688,474 B2
(45) Date of Patent: Jun. 23, 2020

(54) CATALYST FOR DEHYDROGENATION REACTION OF FORMATE AND HYDROGENATION REACTION OF BICARBONATE AND PREPARATION METHOD THEREOF

(71) Applicants: KOREA INSTITUTE OF SCIENCE AND TECHNOLOGY, Seoul (KR); Rutgers University, Piscataway, NJ (US)

(72) Inventors: Chang Won Yoon, Seoul (KR); Hyung Chul Ham, Seoul (KR); Suk Woo Nam, Seoul (KR); Tewodros Asefa, Piscataway, NJ (US); Katherine Koh, Piscataway, NJ (US); Jonghee Han, Seoul (KR); Sung Pil Yoon, Seoul (KR); Hyun Seo Park, Seoul (KR); Mina Jeon, Suwon-si (KR)

(73) Assignees: Korea Institute of Science and Technology, Seoul (KR); Rutgers University, Piscataway, NJ (US)

( * ) Notice: Subject to any disclaimer, the term of this patent is extended or adjusted under 35 U.S.C. 154(b) by 70 days.

(21) Appl. No.: 15/719,692

(22) Filed: Sep. 29, 2017

(65) Prior Publication Data

US 2018/0085738 A1 Mar. 29, 2018

Related U.S. Application Data

(60) Provisional application No. 62/401,304, filed on Sep. 29, 2016.

(51) Int. Cl.

| | | |
|---|---|---|
| *C01B 31/08* | (2006.01) | |
| *B01J 23/44* | (2006.01) | |
| *C01B 3/22* | (2006.01) | |
| *C07C 51/41* | (2006.01) | |
| *B01J 21/18* | (2006.01) | |
| *B01J 35/00* | (2006.01) | |
| *B01J 35/08* | (2006.01) | |
| *B01J 35/10* | (2006.01) | |
| *B01J 37/02* | (2006.01) | |
| *B01J 37/08* | (2006.01) | |
| *C01B 3/00* | (2006.01) | |
| *C07C 51/377* | (2006.01) | |
| *C08K 3/36* | (2006.01) | |
| *B01J 37/00* | (2006.01) | |

(52) U.S. Cl.
CPC ............ *B01J 23/44* (2013.01); *B01J 21/18* (2013.01); *B01J 35/0006* (2013.01); *B01J 35/08* (2013.01); *B01J 35/1023* (2013.01); *B01J 35/1028* (2013.01); *B01J 37/0221* (2013.01); *B01J 37/084* (2013.01); *C01B 3/0015* (2013.01); *C01B 3/22* (2013.01); *C07C 51/377* (2013.01); *C07C 51/41* (2013.01); *C08K 3/36* (2013.01); *B01J 37/0018* (2013.01); *C01B 2203/1041* (2013.01); *C01B 2203/1211* (2013.01); *Y02E 60/328* (2013.01)

(58) Field of Classification Search
CPC ...................................................... B01J 23/44
See application file for complete search history.

(56) References Cited

U.S. PATENT DOCUMENTS

| | | | | |
|---|---|---|---|---|
| 7,220,697 | B2 * | 5/2007 | Pak ..................... | B01J 21/18 423/445 R |
| 7,659,225 | B2 * | 2/2010 | Chen ................... | B01J 21/18 424/405 |
| 7,776,779 | B2 * | 8/2010 | Joo ..................... | B01J 21/18 423/445 R |
| 2015/0166337 | A1 | 6/2015 | Himeda et al. | |
| 2016/0250626 | A1 | 9/2016 | Himeda et al. | |

FOREIGN PATENT DOCUMENTS

| | | |
|---|---|---|
| JP | 2014-508829 A | 4/2014 |
| KR | 10-2016-0010151 A | 1/2016 |
| WO | WO 2012/109212 A2 | 8/2012 |
| WO | WO 2013/111860 A1 | 8/2013 |
| WO | WO 2015/053317 A1 | 4/2015 |

OTHER PUBLICATIONS

Zaidman, B. et al, "Formate Salts as Chemical Carriers in Hydrogen Storage and Transportation", The Hebrew University of Jerusalem, Int. J. Hydrogen Energy, vol. 11, No. 5, 1986, pp. 341-347.
Wiener, Harold. et al., "Palladium-Catalyzed Decomposition of Aqueous Alkali Metal Formate Solutions," Journal of Molecular Catalysis, 35, 1986, pp. 277-284.
Loges, Bjorn. et al, "Controlled Generation of Hydrogen from Formic Acid Amine Adducts at Room Temperature and Application in H2/O2 Fuel Cells", Angew. Chem. Int. Ed. 2008, pp. 3962-3965.
Martis, Martin et al., "Amine-Functionalized MIL-25 with Imbedded Palladium Nanoparticles as an Efficient Catalyst for Dehydrogenation of Formic Acid at Ambient Temperature", The Journal of Physical Chemistry, Oct. 11, 2013, pp. 22805-22810.

(Continued)

*Primary Examiner* — Stuart L Hendrickson
(74) *Attorney, Agent, or Firm* — NSIP Law

(57) ABSTRACT

Provided is a method for preparing a catalyst for a dehydrogenation reaction of formate and a hydrogenation reaction of bicarbonate, the method including: adding a silica colloid to a polymerization step of polymerizing aniline and reacting the resulting mixture to form a poly(silica-aniline) composite; carbonizing the corresponding poly(silica-aniline) composite under an atmosphere of an inert gas; removing silica particles from the corresponding poly(silica-aniline) composite to form a polyaniline-based porous carbon support; and fixing palladium particles on the corresponding polyaniline-based porous carbon support to prepare the catalyst.

4 Claims, 18 Drawing Sheets

(56) References Cited

OTHER PUBLICATIONS

Wang, Zhi-Li. et al., "Facile synthesis of nitrogen-doped graphene supported AuPd—CeO2 nanocomposites with high-performance for hydrogen generation from formic acid at room temperature" The Royal Society of Chemistry, Dec. 20, 2013, pp. 3073-3077.

Jiang, Kun. et al., "Bi-Doped Pd Catalyst: Boosting Room-Temperature Hydrogen Production from Formic Acid-Formate Solutions", Journal of The American Chemical Society, Mar. 17, 2014, pp. 4861-4864.

Song, Fu-Zhan. et al., "Diamine-Alkalized Reduced Graphene Oxide: Immobilization of Sub-2 nm Palladium Nanoparticles and Optimization of Catalytic Activity for Dehydrogenation of Formic Acid", American Chemical Society, Jul. 30, 2015, pp. 5141-5144.

Zhu, Qi-Long. Et al., "Immobilizing Extremely Catalytically Active Palladium Nanoparticles to Carbon Nanospheres: A Weakly-Capping Growth Approach", Journal of American Chemical Society, Aug. 31, 2015, pp. 11743-11748.

\* cited by examiner

CATALYST FOR DEHYDROGENATION REACTION OF FORMATE AND HYDROGENATION REACTION OF BICARBONATE AND PREPARATION METHOD THEREOF

CROSS-REFERENCE TO RELATED APPLICATION

This application claims the benefit of a prior-filed provisional U.S. Patent Application No. 62/401,304, filed on Sep. 29, 2016, and all the benefits accruing therefrom under 35 U.S.C. § 119, the contents of which in its entirety are herein incorporated by reference.

BACKGROUND

1. Field

The present disclosure relates to a new catalyst for a dehydrogenation reaction of formate and a hydrogenation of bicarbonate, and a method for preparing the same. More particularly, the present disclosure relates to a catalyst for a dehydrogenation reaction of formate and a hydrogenation reaction of bicarbonate, which has a high specific surface area, and a method for preparing the same.

2. Description of the Related Art

In order to address concerns about increasing energy and environmental problems associated with production and storage of energy in the future, efficient and sustainable technologies have been extensively studied, and among them, the use of hydrogen through fuel cells attracted significant attention as an alternative to the production of electric energy with fossil fuels. In order to achieve the hydrogen economy based on hydrogen, a safe and innovative hydrogen storage system which is capable of storing a large amount of hydrogen should be developed. For this purpose, metal hydrides, metal-organic frameworks, chemical hydrides, and the like have been proposed as a potential hydrogen storage material over the past several decades. For a chemical hydrogen storage technology for storing hydrogen through chemical bonds using molecules among these various hydrogen storage materials, studies for applying the technology to various fuel cell systems have been continuously performed, and in particular, sodium borohydride and ammonia borane compounds, which are representative chemical hydrogen storage materials, have received much attention partly due to their high gravimetric hydrogen storage capacities and the characteristics capable of releasing hydrogen at a temperature of 100° C. or less, if necessary. However, regeneration processes of waste-fuels produced via dehydrogenation with these kinds of chemicals are energy intensive. Moreover, solid hydrogen energy carriers could potentially have issues associated with their transportation from a storage tank into a dehydrogenation reactor, which further lowers a system efficiency.

A liquid chemical hydrogen storage material has a high volumetric hydrogen storage density as well as, but not necessarily, a high gravimetric hydrogen storage capacity, which secures a high economic efficiency particularly for stationary applications. In addition, a liquid hydrogen storage material has a high potential as an energy carrier because hydrogen is relatively easily stored and conveyed. In this context, formic acid ($HCO_2H$) and liquid compounds related to the acid have received much attention as a reversible hydrogen storage material, and catalyst systems based on various transition metals for a selective dehydrogenation reaction of formic acid at a temperature of 60° C. or less have been developed. However, studies for again regenerating carbon dioxide, which is a waste fuel produced after dehydrogenation of formic acid, into formic acid through a hydrogenation reaction with heterogeneous catalysts have been little reported, and the development of a catalyst system capable of effectively facilitating the corresponding reaction has been studied.

As a strategy for improving the reversibility of the formic acid system, it has been recently reported that a reversible reaction of formate/bicarbonate ($HCO_2^-/HCO_3^-$) is achievable and the formate/bicarbonate system can be employed as a reversible hydrogen energy carrier (a dehydrogenation reaction of formate: $HCO_2^- + H_2O \rightarrow H_2 + HCO_3^-$; a hydrogenation reaction of bicarbonate: $H_2 + HCO_3^- \rightarrow H_2O + HCO_2^-$). In the case of an aqueous formate ($HCO_2^-$) solution, the reaction may be performed without producing carbon monoxide (CO) which is detrimental to a catalyst located at the surface of a polymer electrolyte membrane fuel cell (PEMFC) during the dehydrogenation reaction, and simultaneously, bicarbonate ($HCO_3^-$), which is a waste fuel produced after the generation of hydrogen, can be more widely used as a reversible hydrogen storage system for storing and transporting hydrogen energy because a hydrogenation reaction of bicarbonate is performed more easily than a hydrogenation of formate. However, there is a need for studies on a heterogeneous catalyst for inter-conversion of the above-described $HCO_2^-/HCO_3^-$ reaction. For catalyst development relevant to dehydrogenation and hydrogenation reactions involving formic acid and the like, it has been recently reported that a carbon supported catalyst (e.g., Pd/C) is superior in terms of selectivity, reversibility, catalytic activity, and the like than homogeneous catalysts.

Meanwhile, it was currently revealed that doping of carbon materials with a heteroatom (for example, nitrogen or boron) can contribute to not only changing physical, chemical, or structural properties of the carbon materials, but also improving the catalytic activity of a heterogeneous catalyst such as Pd. However, in spite of this fact, a catalyst including a carbon support doped with a heteroatom has not been reported as a use for a $HCO_2^-/HCO_3^-$ reversible reaction.

REFERENCES OF THE RELATED ART

Non-Patent Documents

Wiener, H.; Sasson, Y.; Blum, J. J. Mol. Catal. 1986, 35, 277.
Zaidman, B.; Wiener, H.; Sasson, Y. Int. J. Hydrog. Energy 1986, 11, 341.

SUMMARY

Embodiments of the present disclosure have been made in an effort to provide a catalyst for a dehydrogenation reaction of formate and a hydrogenation reaction of bicarbonate, which has a high specific surface area, and a method for preparing the same.

In an embodiment of the present disclosure, provided is a method for preparing a catalyst for a dehydrogenation reaction of formate and a hydrogenation reaction of bicarbonate, the method including: adding a silica colloid to a polymerization step of polymerizing aniline to form polyaniline and reacting the resulting mixture to form a poly (silica-aniline) composite; carbonizing the poly(silica-aniline) composite under an atmosphere of an inert gas; removing silica particles from the poly(silica-aniline) composite to form a polyaniline-based porous carbon support; and fixing palladium particles on the polyaniline-based porous carbon support to prepare the catalyst.

In an exemplary embodiment, the catalyst may be represented by the following Chemical Formula 1.

Pd/PDMC-T-X        [Chemical Formula 1]

(In Chemical Formula 1, Pd and PDMC mean palladium and a polyaniline-based porous carbon support, respectively, T means a temperature in the carbonization step, and X is a weight (g) of the silica colloid added per 0.02 mmol of aniline in the polymerization step of polyaniline).

In an exemplary embodiment, T in Chemical Formula 1 may be within a range of 500 to 1,000° C.

In an exemplary embodiment, T in Chemical Formula 1 may be within a range of 790 to 810° C.

In an exemplary embodiment, X in Chemical Formula 1 may be within a range of 4 to 18 g.

In an exemplary embodiment, X in Chemical Formula 1 may be within a range of 13 to 17 g.

In an exemplary embodiment, a specific surface area of the catalyst may be proportional to a mixed amount of the silica colloid.

In an exemplary embodiment, the catalyst may have a specific surface area of 500 to 1,200 $(m^2 \cdot g^{-1})$.

In another exemplary embodiment of the present disclosure, provided is a catalyst for a dehydrogenation reaction of formate and a hydrogenation reaction of bicarbonate, which includes a polyaniline-based porous carbon support, in which palladium particles are fixed, and has a specific surface are of 500 to 1,200 $(m^2 \cdot g^{-1})$, as a catalyst for a dehydrogenation reaction of formate and hydrogenation reaction of bicarbonate.

In an exemplary embodiment, the polyaniline-based porous carbon support may be a reaction product of a reaction of removing silica particles from a carbon composite produced via carbonization of a poly(silica-aniline) composite, and the poly(silica-aniline) composite may be a reaction product produced by mixing and reacting a silica colloid in a polymerization step of polyaniline.

In an exemplary embodiment, the catalyst may have a spherical structure.

In another embodiment of the present disclosure, provided is a method for releasing and storing hydrogen via a dehydrogenation reaction of formate and a hydrogenation of bicarbonate using the catalyst.

The catalyst for a dehydrogenation of formate and a hydrogenation reaction of bicarbonate according to an embodiment of the present disclosure may have a high specific surface area and a high catalytic activity. Accordingly, it is possible to exhibit a very high activity for a dehydrogenation reaction of formate and a hydrogenation reaction of bicarbonate.

According to a method for preparing the catalyst for a dehydrogenation reaction of formate and a hydrogenation reaction of bicarbonate according to an embodiment of the present disclosure, provided is an optimal condition in a process of preparing a catalyst, which is capable of a producing a catalyst having excellent catalytic activity.

DETAILED DESCRIPTION

In the present specification, the term "poly(silica-aniline) composite" means a product produced by mixing a silica colloid together, and then reacting the resulting mixture in a polymerization step of polymerizing aniline to form polyaniline. On the far left side of FIG. 1, a schematic structure of the poly(silica-aniline) composite is shown (shown as polyaniline (PANI)-$SiO_2$).

Hereinafter, embodiments of the present disclosure will be described in detail with reference to accompanying drawings. Embodiments of the present disclosure have been described with reference to accompanying drawings, but have been described for illustration, and the technical spirit of the present disclosure and the configuration and application thereof are not limited thereby.

Method for Preparing Catalyst for Dehydrogenation Reaction of Formate and Hydrogenation Reaction of Bicarbonate In an embodiment of the present disclosure, provided is a method for preparing a catalyst for a dehydrogenation reaction of formate and a hydrogenation reaction of bicarbonate, the method including: adding a silica colloid to a polymerization step of polymerizing aniline to form polyaniline and reacting the resulting mixture to form a poly (silica-aniline) composite; carbonizing the poly(silica-aniline) composite under an atmosphere of an inert gas; removing silica particles from the poly(silica-aniline) composite to form a polyaniline-based porous carbon support; and fixing the palladium particles on the polyaniline-based porous carbon support to prepare the catalyst.

Figure 1:
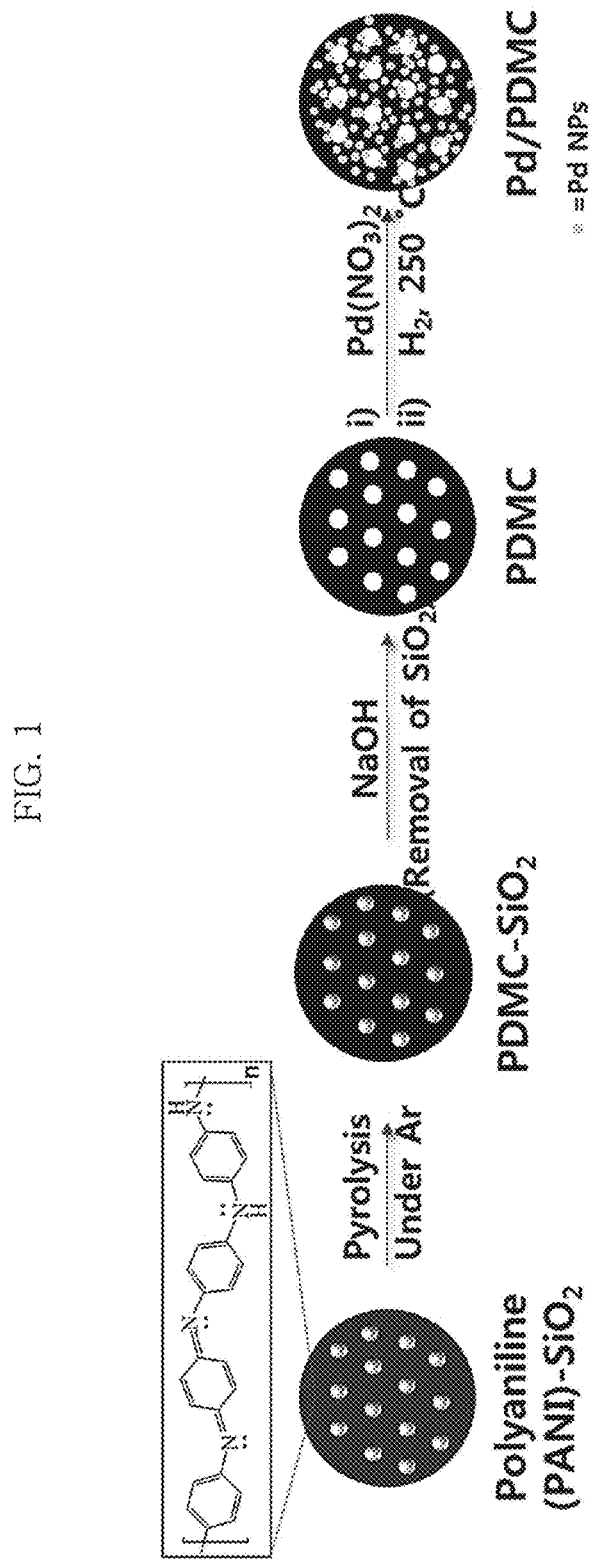
FIG. 1 is a schematic view showing a method for preparing a catalyst according to an embodiment of the present disclosure.
Figure 2A:
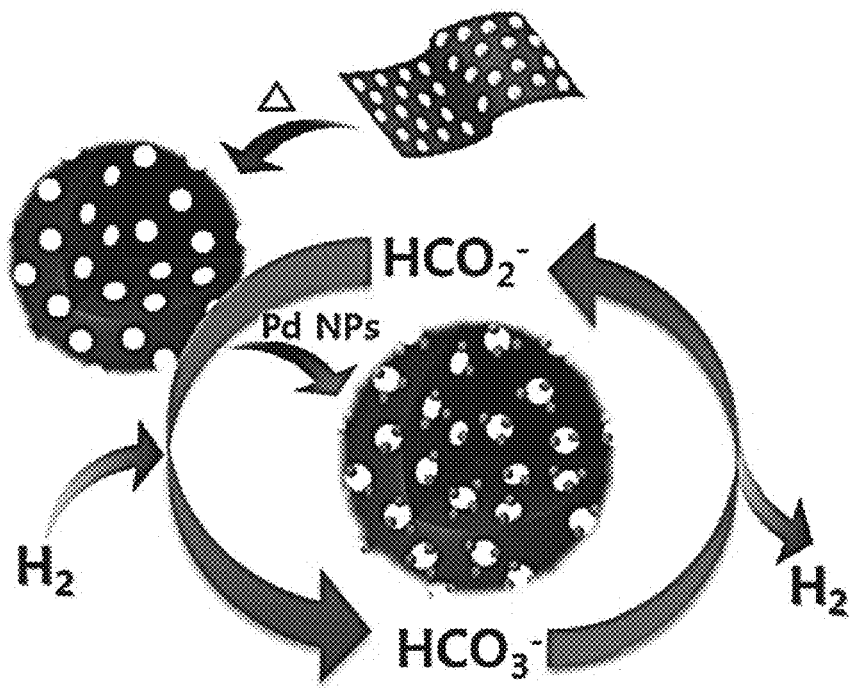
FIGS. 2A and 2B show a schematic view of a dehydrogenation reaction of formate and a hydrogenation reaction of bicarbonate, in which the catalyst prepared according to an embodiment of the present disclosure is used, and the reaction mechanisms thereof, respectively.
Figure 2B:
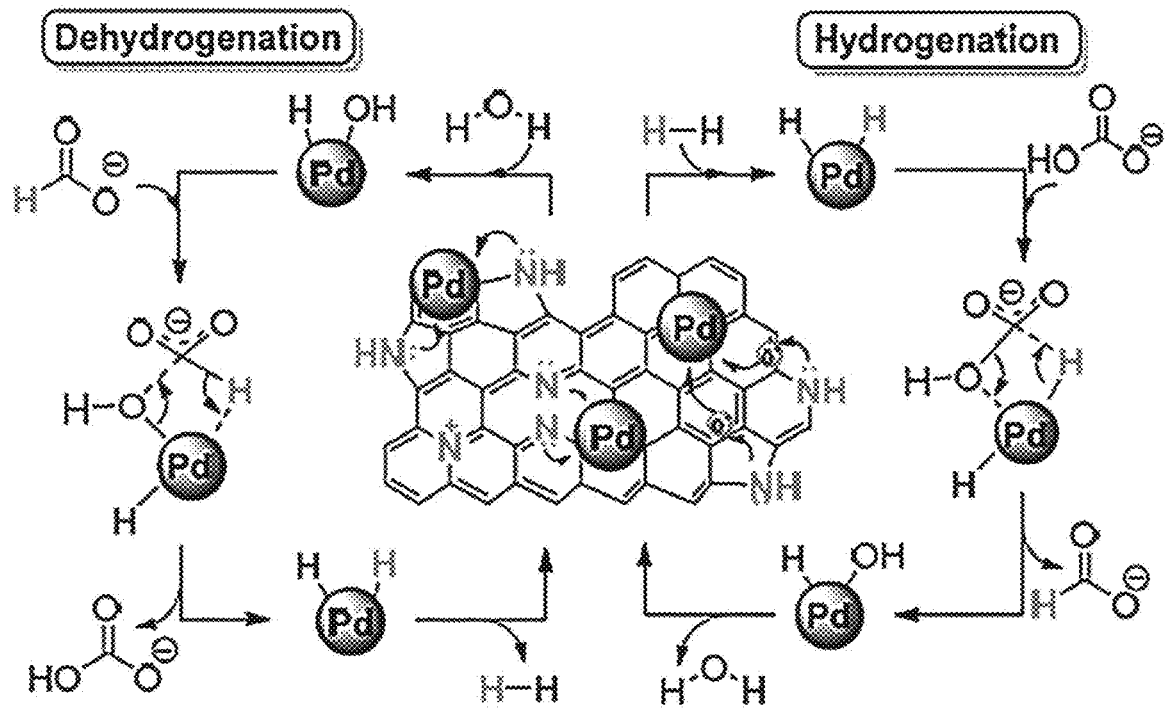
Figure 3A:
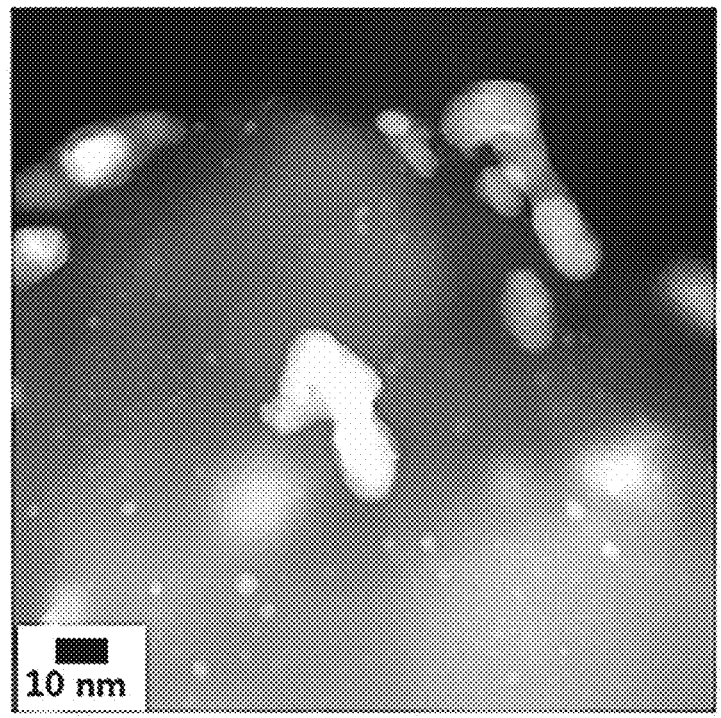
FIGS. 3A and 3B are photographs showing the structural change of a catalyst particle according to Comparative Example 1.
Figure 3B:
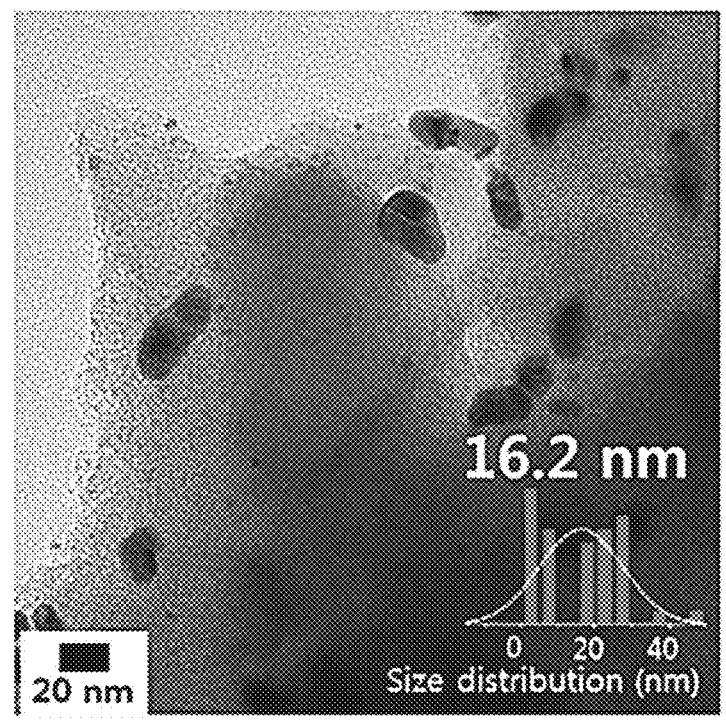
Figure 4A:
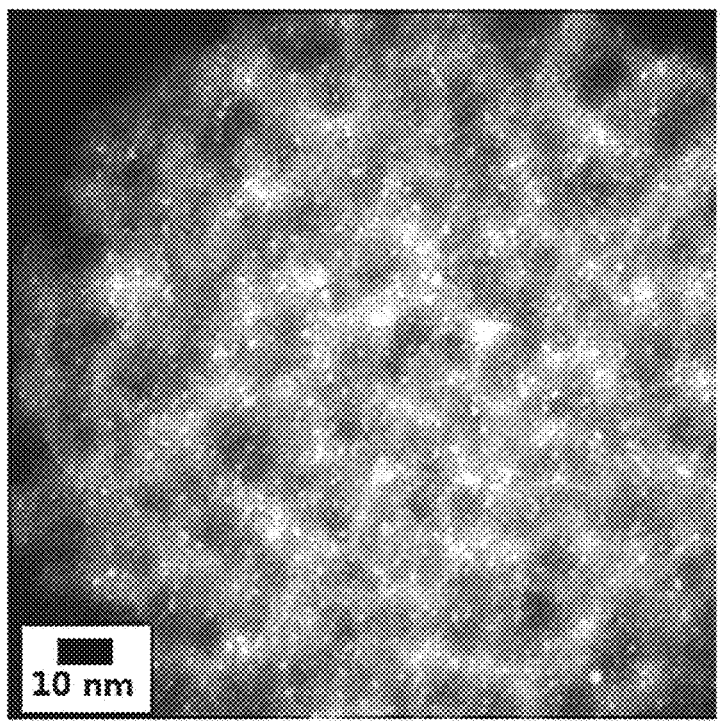
FIGS. 4A and 4B are photographs showing the structural change of a catalyst particle according to Example 1.
Figure 4B:
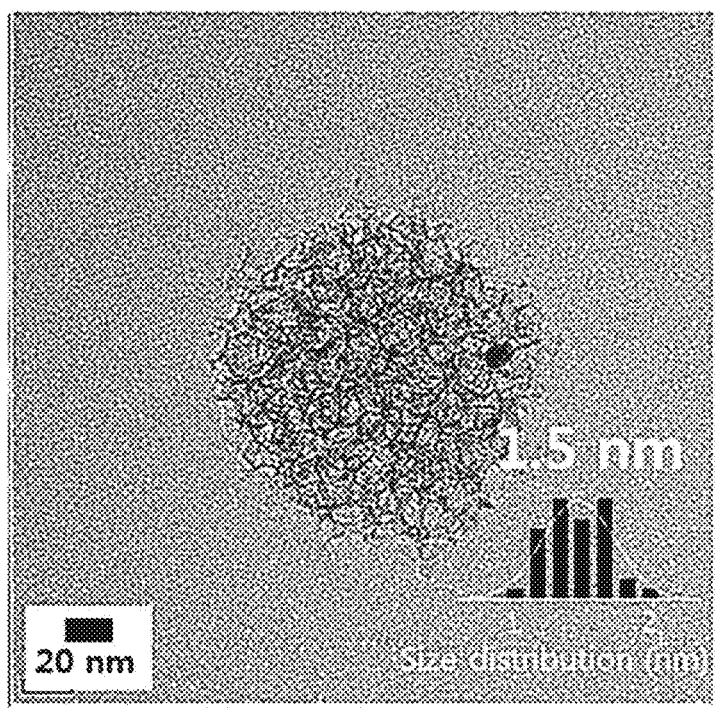
Figure 5A:
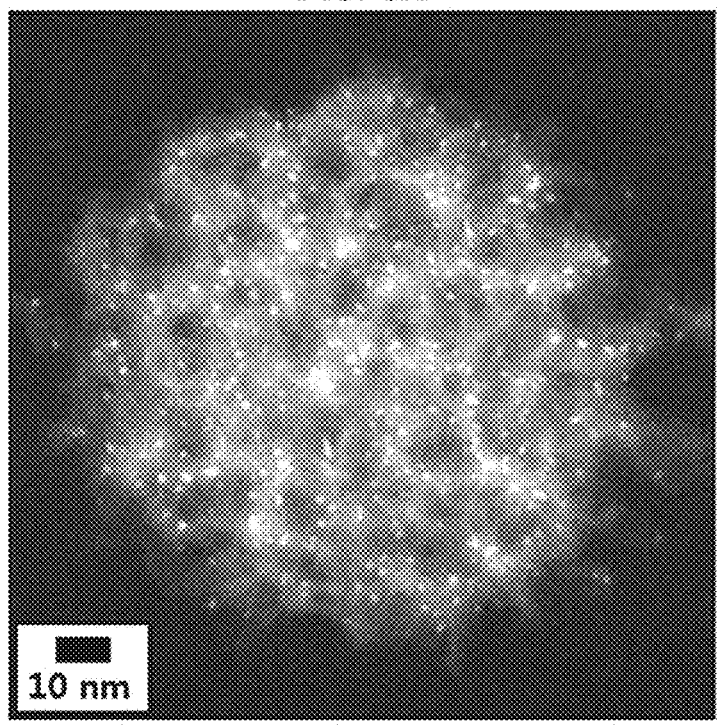
FIGS. 5A and 5B are photographs showing the structural change of a catalyst particle according to Example 2.
Figure 5B:
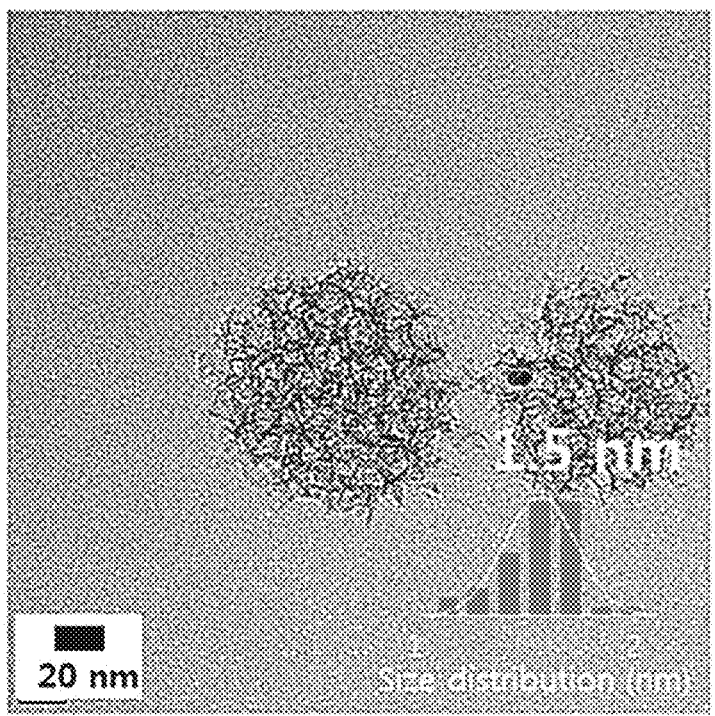
Figure 6A:
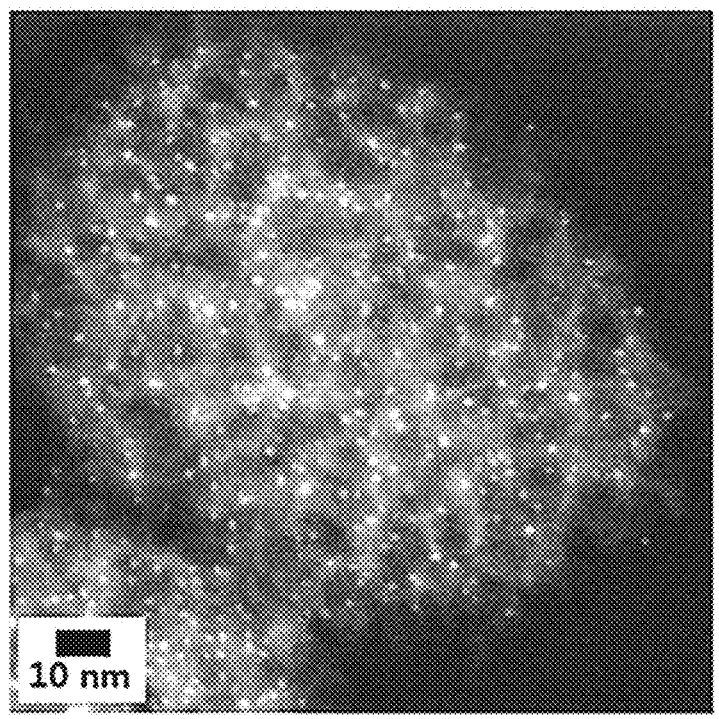
FIGS. 6A and 6B are photographs showing the structural change of a catalyst particle according to Example 3.
Figure 6B:
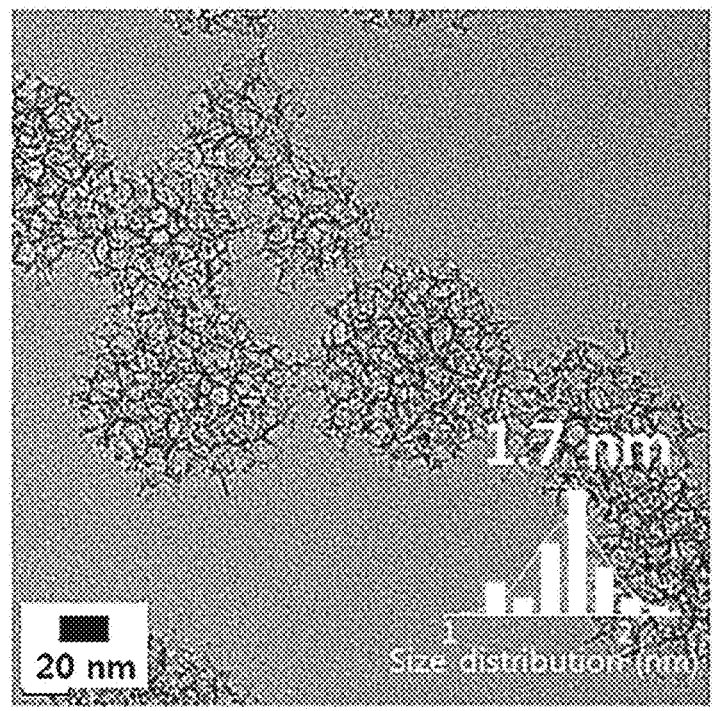
Figure 7A:
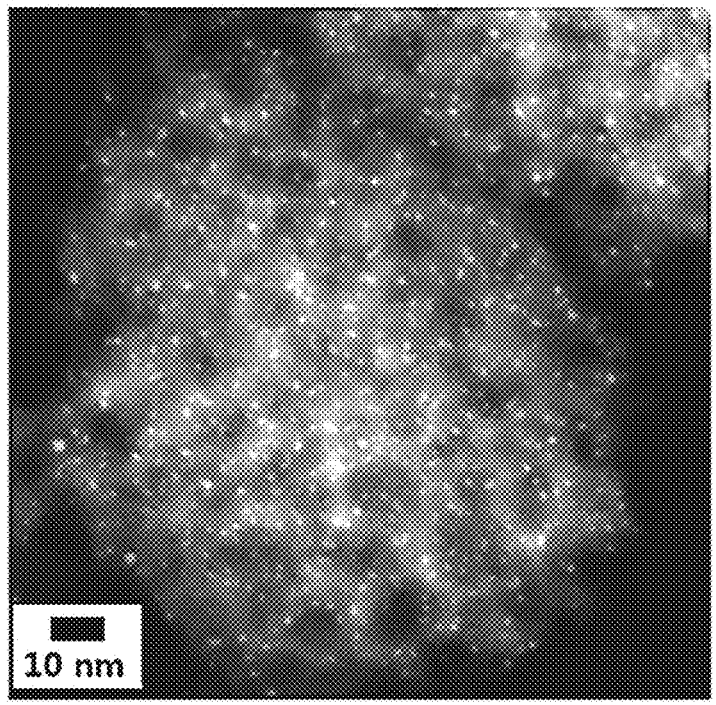
FIGS. 7A and 7B are photographs showing the structural change of a catalyst particle according to Example 7.
Figure 7B:
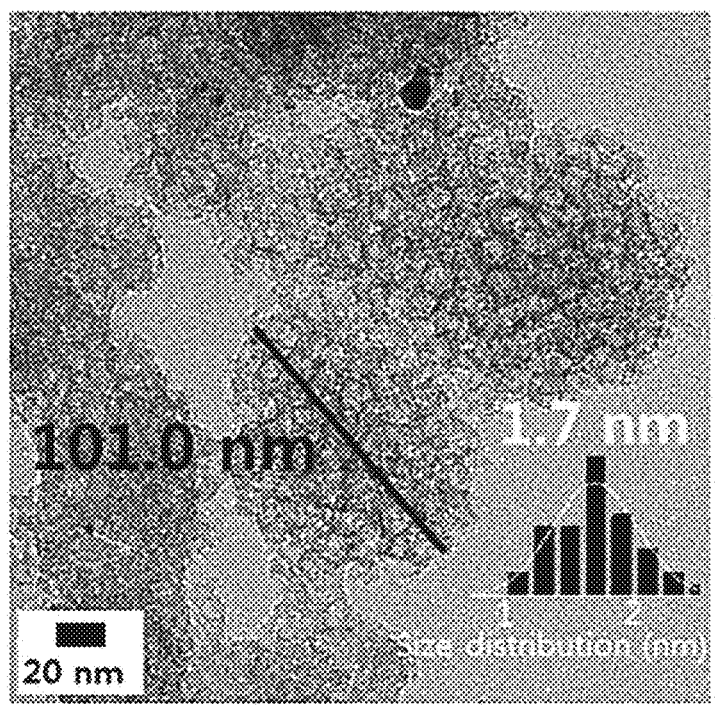
Figure 8A:
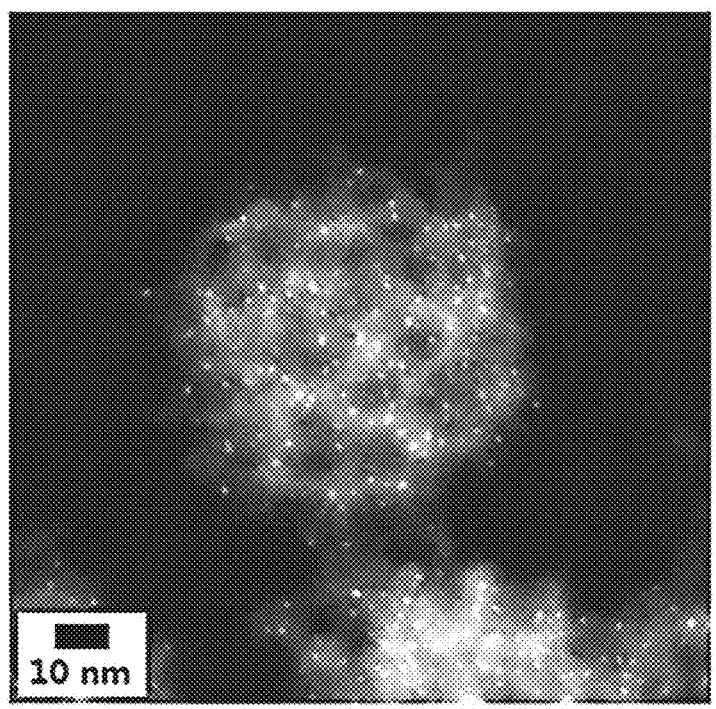
FIGS. 8A and 8B are photographs showing the structural change of a catalyst particle according to Example 6.
Figure 8B:
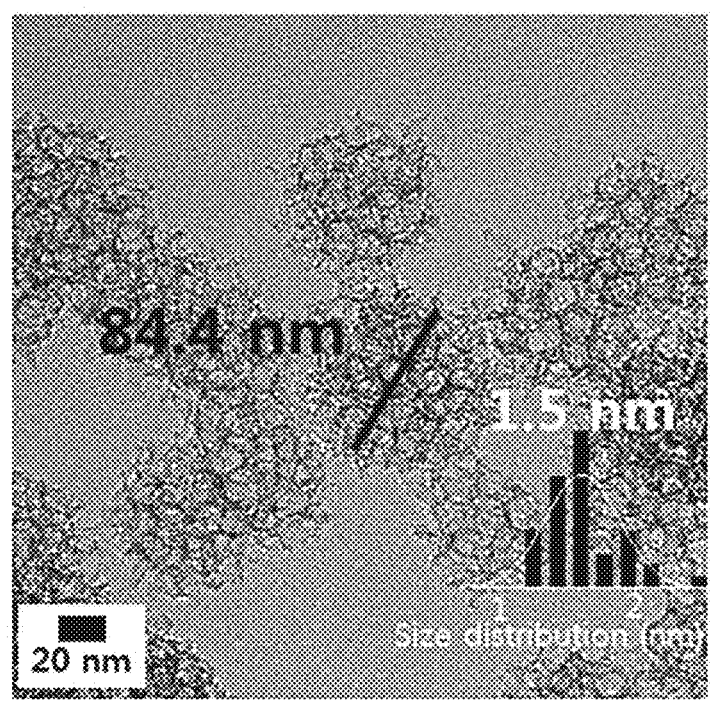
Figure 9A:
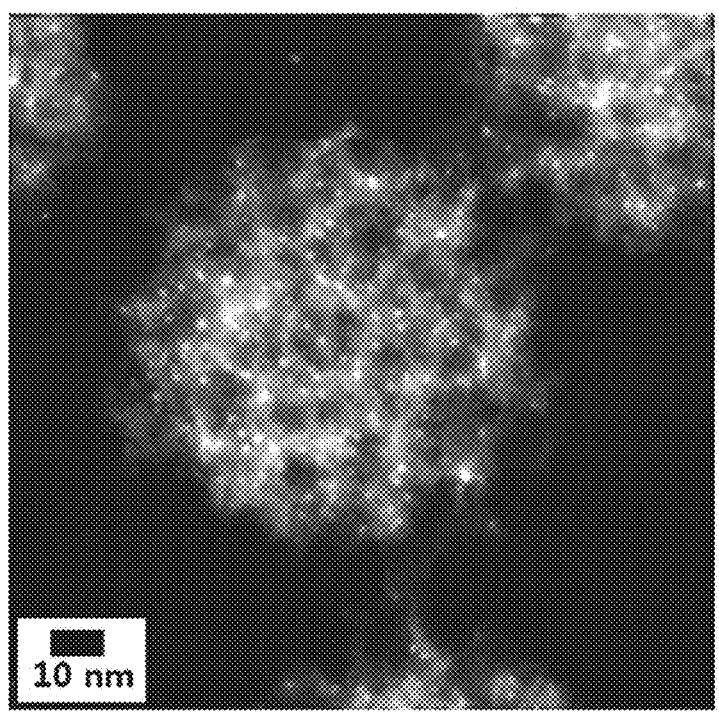
FIGS. 9A and 9B are photographs showing the structural change of a catalyst particle according to Example 5.
Figure 9B:
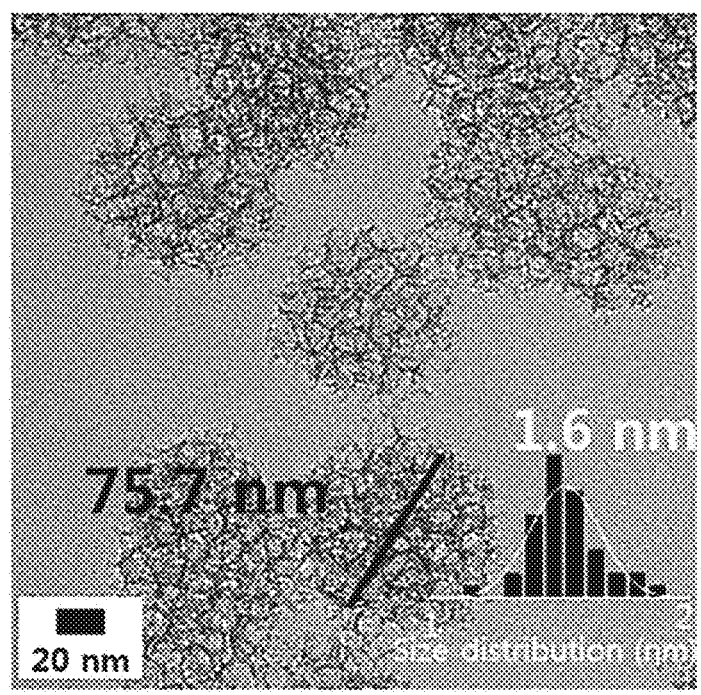
Figure 10A:
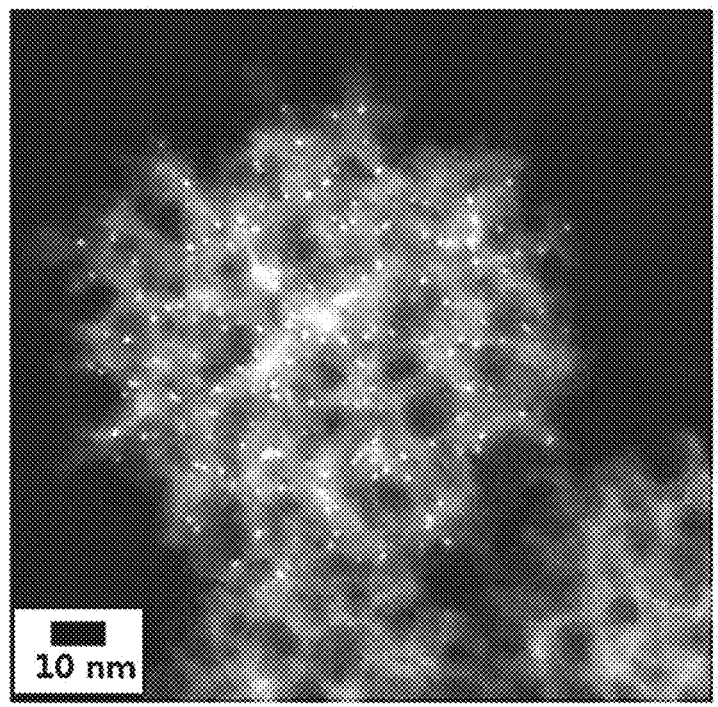
FIGS. 10A and 10B are photographs showing the structural change of a catalyst particle according to Example 4.
Figure 10B:
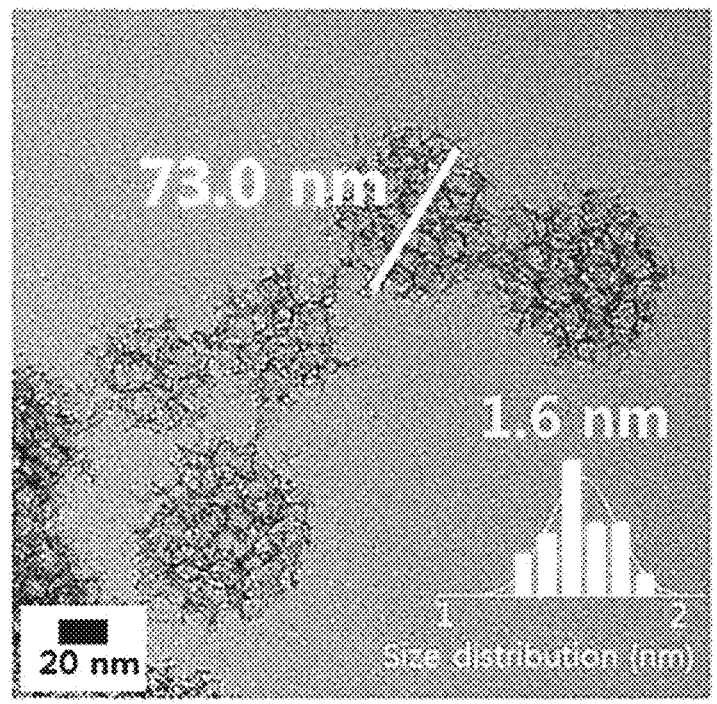
Figure 11A:
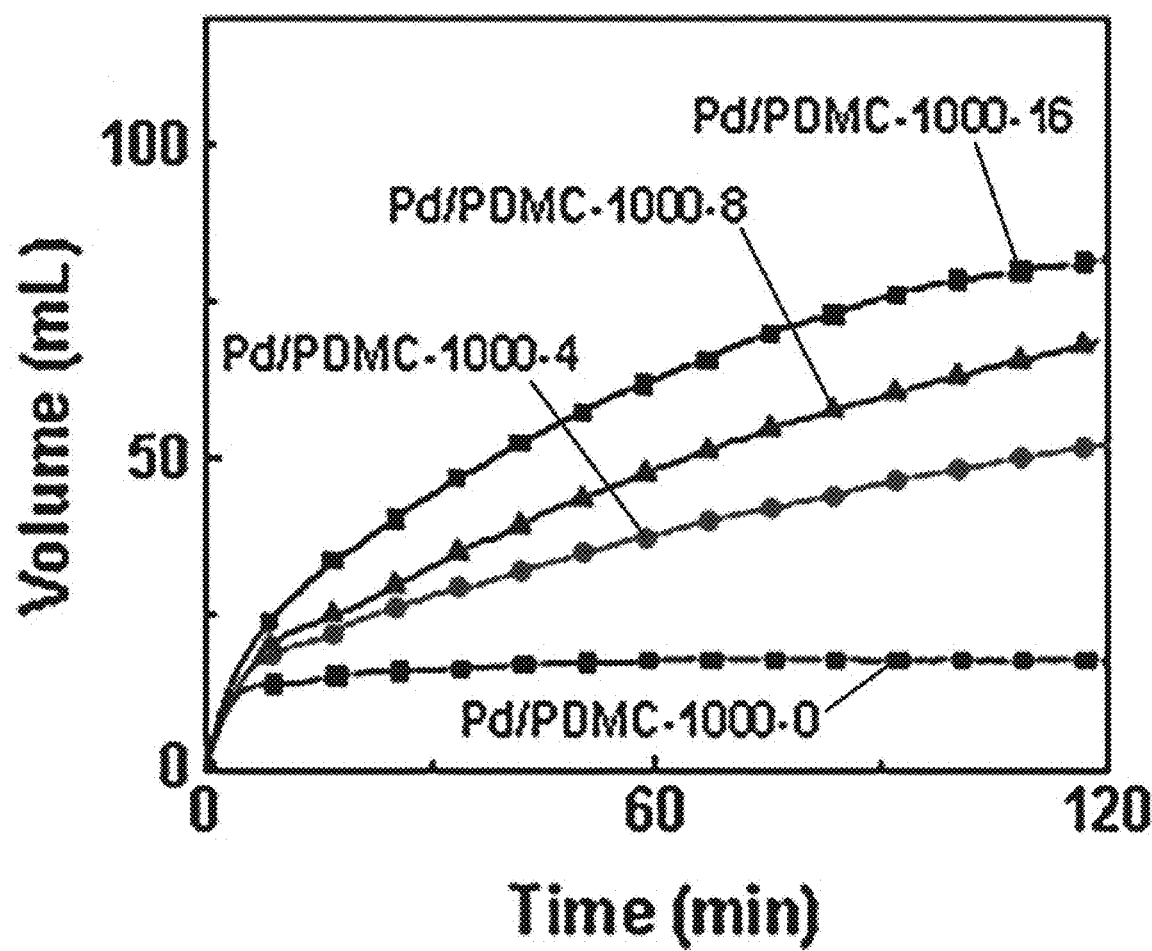
FIGS. 11A and 11B are graphs showing the change in activity of the catalyst according to the change in amount of silica.
Figure 11B:
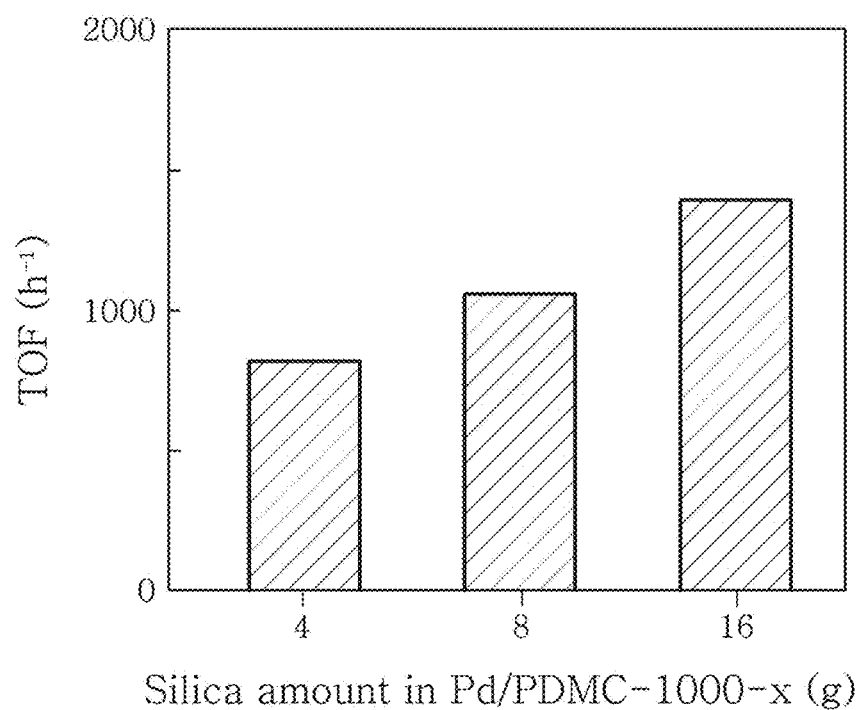
Figure 11C:
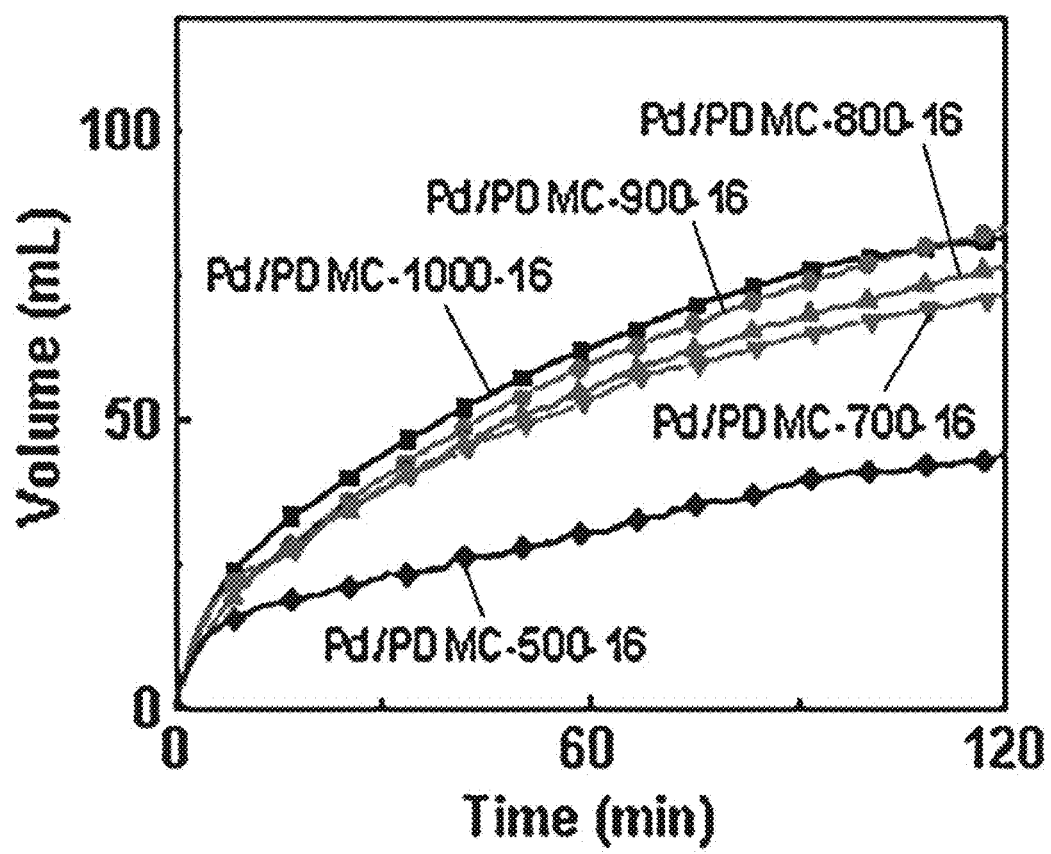
FIGS. 11C and 11D are graphs showing the change in activity of the catalyst according to the change in temperature in the carbonization step.
Figure 11D:
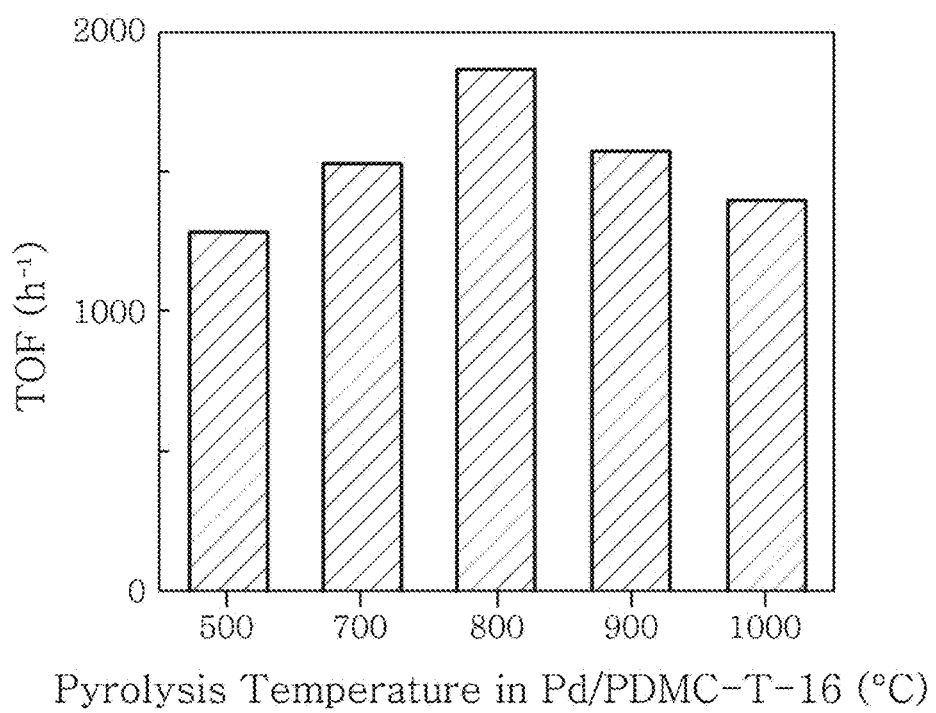

FIG. 1 is a schematic view showing a method for preparing a catalyst according to an embodiment of the present disclosure. Hereinafter, the preparation method will be examined in detail with reference to FIG. 1.

First, a silica colloid is added to a polymerization step of polymerizing aniline to form polyaniline, and the resulting mixture is reacted to form a poly(silica-aniline) composite.

Specifically, in the polymerization step of aniline which is a precursor for polyaniline, aniline is slowly added to a solution including a silica colloid and the resulting mixture is subjected to polymerization reaction to prepare a poly(silica-aniline) composite.

In an exemplary embodiment, the silica colloid may be one or more selected from the group consisting of silica sol, silica gel, silica nanoparticles, and the like.

In an exemplary embodiment, in the addition step, the silica colloid may be added in an amount of 4 g to 18 g, and preferably 13 g to 17 g, per 0.02 mol of aniline. When the silica particles are mixed in an amount of less than 4 g, a catalyst to be prepared later may be prepared so as to have a small specific surface area, and when the silica particles are mixed in an amount of more than 18 g, a porous catalyst structure may not be properly formed due to the aggregation phenomenon of silica.

In an exemplary embodiment, the specific surface area of the catalyst may be increased in proportion to an amount of silica colloid added within a range not degrading the activity of a catalyst finally produced by the silica colloid.

The mixing reaction may be performed for about 18 to 24 hours, and accordingly, a poly(silica-aniline) composite produced by polymerizing a mixture of aniline with silica may be prepared.

Subsequently, the poly(silica-aniline) composite is carbonized under an atmosphere of an inert gas.

Specifically, under an atmosphere of an inert gas such as nitrogen ($N_2$) or argon (Ar), the poly(silica-aniline) composite may be subjected to heat treatment to carbonize silica of the poly(silica-aniline) composite.

In an exemplary embodiment, the carbonization process may be performed according to a single process performed at a temperature of 500 to 1,000° C. for 3 to 8 hours, and specifically, may be performed within a temperature range of 790 to 810° C.

In contrast, in an exemplary embodiment, the carbonization process may be performed dividedly in two steps of a first carbonization process and a second carbonization process.

In an Example, the first carbonization process is a carbonization process performed at a relatively low temperature of about 200 to 400° C. for 2 to 4 hours, and may be a step of preventing a poly(silica-aniline) composite from being structurally damaged.

In an exemplary embodiment, the second carbonization process is performed at a relatively high temperature for 1 to 4 hours as a full-fledged carbonization process, and at this time, a poly(silica-aniline) composite may be carbonized to form a silica-nitrogen-carbon nano composite.

In an Example, the second carbonization process may be performed within a temperature range of 500 to 1,000° C., preferably 700 to 900° C., and more preferably 790 to 810° C. When the second carbonization process is performed at a temperature of less than 500° C., the composite is not sufficiently carbonized, so that an aromatic ring by a formed intermolecular cross-linkage or double bond of the carbon structure is not properly formed, and as a result, a desired graphitic carbon structure cannot be obtained, and when the second carbonization process is performed at a temperature of more than 1,000° C., a structural defect of a poly(silica-aniline) composite to be carbonized may be caused.

Meanwhile, when the second carbonization process is performed at a temperature of about 800° C., the activity of a catalyst to be finally formed may be more improved, and as the carbonization process is performed, the improved activity is because the structure including nitrogen in the poly(silica-aniline) composite is pyrrolinized or pyridinized Subsequently, silica particles are removed from the carbonized poly(silica-aniline) composite to form a polyaniline-based porous carbon support.

Specifically, the poly(silica-aniline) composite is impregnated in a solution such as sodium hydroxide and silica particles are removed from the carbonized poly(silica-aniline) composite to form a polyaniline-based porous carbon support. As the silica particles are removed from the poly(silica-aniline) composite, pores may be formed at sites in which the silica particles used to be present.

Thereafter, the polyaniline-based porous carbon support may be filtered and dried to prepare a polyaniline-based porous carbon support in the form of powder.

Finally, palladium particles are fixed on the polyaniline-based porous carbon support to prepare a catalyst including a porous carbon support in which palladium particles are impregnated.

Specifically, after the polyaniline-based porous carbon support is dispersed in an aqueous solution, a palladium precursor is added in an amount of 1 to 5 wt % (preferably 1 to 3 wt %) based on the total weight of the support thereto, and then the resulting mixture is stirred at normal temperature for 2 to 6 hours, and then dried. Accordingly, palladium particles or palladium ions may be impregnated in pores of the polyaniline-based porous carbon support.

In an exemplary embodiment, the palladium precursor may include one or more selected from the group consisting of aqueous $Pd^{2+}$-based compounds, such as $Pd(NO_3)_2 \cdot 2H_2O$, $PdCl_2$, $Pd(OAc)_2$, and $PdI_2$.

Meanwhile, if palladium ions are impregnated in the support, a catalyst may be finally prepared by reducing $Pd^{2+}$ ions impregnated in the support to Pd through an additional reduction process.

In an exemplary embodiment, the catalyst may be represented by the following Chemical Formula 1.

$$\text{Pd/PDMC-T-X} \qquad \text{[Chemical Formula 1]}$$

In Chemical Formula 1, Pd and PDMC mean palladium and a polyaniline-based porous carbon support, respectively, T means a temperature in the carbonization step, and X is a weight (g) of the silica colloid added per 0.02 mmol of aniline in the polymerization step of polyaniline.

In Chemical Formula 1, T may have a value within a range of 500 to 1,000° C., and a value within a temperature range of preferably 700 to 900° C., and more preferably 790 to 810° C.

Further, in Chemical Formula 1, X may have a value within a range of 4 g to 18 g, and preferably 13 g to 17 g.

In an exemplary embodiment, the palladium particles may have a diameter of about 1.0 to 2.0 nm, preferably 1.5 to 1.7 nm. When the particle particles have a relatively small diameter as described above, the particles may be widely dispersed and impregnated in the support, and as catalyst active sites capable of being reacted are increased, the activity of the catalyst may be increased as compared to an equal amount of palladium.

In an exemplary embodiment, the specific surface area of the catalyst may be varied by conditions such as a temperature condition of the carbonization process of the poly (silica-aniline) composite and the content of silica colloid to be added in the polymerization step of aniline.

For example, as the content of silica colloid is increased, the specific surface area of the catalyst may be increased.

Accordingly, the aforementioned conditions and the like may be optimized to prepare a catalyst for a dehydrogenation reaction of formate and a hydrogenation reaction of bicarbonate, which has a high specific surface area.

In an exemplary embodiment, the catalyst may have a specific surface area of about 500 to 1,200 $(m^2 \cdot g^{-1})$, preferably 800 to 1,200 $(m^2 \cdot g^{-1})$, and more preferably 900 to 1,100 $(m^2 \cdot g^{-1})$. The reason that the catalyst has a wide specific surface area as described above is because pores are formed in the support by leaching of the silica colloid, and the specific surface area may be adjusted according to the amount of silica colloid initially introduced. The important reason that the catalyst has a wide specific surface area is because palladium nanoparticles having a much smaller size may be uniformly dispersed on the entire support by a wide specific surface area of the support, and it is possible to expect high catalytic activity because much more catalyst active sites are formed accordingly.

As described above, the catalyst prepared by the method is prepared so as to have a high specific surface area and a structure which easily provides electrons to palladium, may be usefully utilized for a dehydrogenation reaction of formate and a hydrogenation of bicarbonate, and may also be excellently used in a secondary battery including the same.

Catalyst for Dehydrogenation Reaction of Formate and Hydrogenation Reaction of Bicarbonate In another exemplary embodiment of the present disclosure, provided is a catalyst for a dehydrogenation reaction of formate and a hydrogenation reaction of bicarbonate, which includes a polyaniline-based porous carbon support, in which palladium particles are fixed, and has a specific surface are of 500 to 1,200 $(m^2 \cdot g^{-1})$, as a catalyst for a dehydrogenation reaction of formate and hydrogenation reaction of bicarbonate. Since the catalyst is a catalyst prepared by the above-described method for preparing a catalyst, the description on a configuration which is substantially the same as or similar to the method for preparing a catalyst will be omitted.

In an exemplary embodiment, the polyaniline-based porous carbon support may be a reaction product of a reaction of removing silica particles from a carbon composite produced via carbonization of a poly(silica-aniline) composite (i.e., a reaction product via carbonization of a poly(silica-aniline) composite), and the poly(silica-aniline) composite may be a reaction product produced by mixing and reacting a silica colloid in the polymerization step of polyaniline.

In an exemplary embodiment, the catalyst has a spherical structure, and may be represented by the following Chemical Formula 1.

Pd/PDMC-T-X      [Chemical Formula 1]

In Chemical Formula 1, Pd and PDMC mean palladium and a polyaniline-based porous carbon support, respectively, T means a temperature in the carbonization step and a temperature within a range of 500 to 1,000° C., and X is a weight (g) of the silica colloid added per 0.02 mol of aniline in the polymerization step of polyaniline, and may be an integer within a range of 4 to 18 (g).

The catalyst according to the present disclosure has two or more advantages.

First, since the support of the catalyst include pores formed on the surface thereof by using a silica colloid, the surface area of the support may be maximized. Accordingly, when metal particles such as palladium are later impregnated, the catalyst active sites of palladium to be impregnated may be maximized, and the activity of the catalyst may be improved accordingly.

Further, a region in which nitrogen is included in the catalyst has a pyridinized or pyrrolinized structure, and since the structure is advantageous for providing electrons, nitrogen in the pyridinized or pyrrolinized structure easily provides electrons to palladium particles. Accordingly, since the catalytic activity may be more imparted to palladium particles, the activity of the catalyst including the same may be finally improved.

Accordingly, when the dehydrogenation reaction of formate and the hydrogenation of bicarbonate are performed by using the catalyst, the yield may be improved.

Hereinafter, the present disclosure will be described in more detail through Examples. These Examples are only for exemplifying the present disclosure, and it will be obvious to those skilled in the art that the scope of the present disclosure is not interpreted to be limited by these Examples.

EXAMPLES

Example 1

(1) After 0.2 mol of APS $(NH_4)_2S_2O_8$ was added to 100 mL of an aqueous solution in which a 1.0 M formic acid was dissolved at 2° C., the resulting mixture was stirred until being completely dissolved, and then 4 g of Ludox® HS-40 silica colloid (40 wt % in $H_2O$) was slowly added thereto under stirring, and then 20 mmol of aniline was slowly added thereto. Thereafter, the resulting mixture was stirred at 2 to 5° C. for 24 hours.

(2) Thereafter, centrifugation was performed at 15,000 rpm for about 20 minutes, then the supernatant was discarded, distilled water was again added thereto, and then after centrifugation was performed at 15,000 rpm for 30 minutes, the process was repeated three times. Subsequently, ethanol was added to the solution, and then centrifugation was performed at 15,000 rpm for 20 minutes, and the process was repeated two times. Thereafter, the resulting product was dried, and then a poly(silica-aniline) composite in a form of powder was obtained.

(3) Subsequently, the poly(silica-aniline) composite was subjected to heat treatment under an atmosphere of an inert gas (Ar or $N_2$), and specifically, after the temperature was increased at a speed of 1° C./min, reached to 300° C., and then maintained for 3 hours, the temperature was reached to 1,000° C. at a speed of 10° C./min, and then maintained for 2 hours.

(4) Subsequently, the carbonized poly(silica-aniline) composite was impregnated in a 1 M aqueous NaOH solution, and then maintained at 100° C. for 24 hours to remove the silica colloid. Thereafter, a polyaniline-based porous carbon support in a form of powder was prepared through filtering and drying processes.

(5) Thereafter, the polyaniline-based porous carbon support was dispersed in the aqueous solution, then a palladium precursor $(Pd(NO_3) \cdot 2H_2O)$ was added in a desired amount (1 to 3 wt % of Pd compared to the support) thereto, and then the resulting mixture was stirred at normal temperature for 3 hours, and then filtered and dried. Thereafter, a catalyst in a form of powder was obtained by reducing $Pd^{2+}$ to $Pd(0)$ at 250° C. while flowing a hydrogen gas.

Example 2

The catalyst was prepared by performing the same process as in Example 1, except that 8 g of a silica colloid was added instead of 4 g of Ludox® HS-40 silica colloid.

Example 3

The catalyst was prepared by performing the same process as in Example 1, except that 16 g of a silica colloid was added instead of 4 g of Ludox® HS-40 silica colloid.

Example 4

The catalyst was prepared by performing the same process as in Example 3, except that the temperature in the heat treatment step (3) was reached to 900° C.

Example 5

The catalyst was prepared by performing the same process as in Example 3, except that the temperature in the heat treatment step (3) was reached to 800° C.

Example 6

The catalyst was prepared by performing the same process as in Example 3, except that the temperature in the heat treatment step (3) was reached to 700° C.

Example 7

The catalyst was prepared by performing the same process as in Example 3, except that the temperature in the heat treatment step (3) was reached to 500° C.

Example 8

The catalyst was prepared by performing the same process as in Example 5, except that 94 µmol/g of palladium was impregnated in the support.

Comparative Example 1

The catalyst was prepared by performing the same process as in Example 1, except that the Ludox® HS-40 silica colloid was not added at all.

Comparative Example 2

As a comparative example, a Pd/C catalyst (Sigma-Aldrich, 10 wt. %) was used.

Experimental Example 1

The surface characteristics of the catalysts prepared in Comparative Example 1 and Examples 1 to 3 were measured, and are shown in Table 1. Further, each surface area of the catalysts was measured by an electron microscope, and is shown in FIGS. 3A to 6B.

TABLE 1

| | Sample | Content (g) of silica colloid | $A_{BET}$ ($m^2 \cdot g^{-1}$) | $D_{BJH}$ (nm) | V ($cm^3 \cdot g^{-1}$) | Metal loading/×$10^{-1}$ mmol/$g_{cat}$ | Average size of Pd (nm) |
|---|---|---|---|---|---|---|---|
| Comparative Example 1 | Pd/PDMC-1000-0 | 0 g | 260 | 2.5 | 0.2 | 0.7 | 16.2 |
| Example 1 | Pd/PDMC-1000-4 | 4 g | 817 | 7.4 | 1.5 | 2.3 | 1.5 |
| Example 2 | Pd/PDMC-1000-8 | 8 g | 919 | 8.0 | 1.8 | 2.0 | 1.5 |
| Example 3 | Pd/PDMC-1000-16 | 16 g | 994 | 9.7 | 2.4 | 1.8 | 1.7 |

When Table 1 and FIGS. 3A to 6B were examined, it could be confirmed that as the amount of silica colloid was increased under the same conditions, the specific surface area of the catalyst was improved. Further, it could be confirmed that as the surface area of the support was increased, Pd nanoparticles were uniformly dispersed in small sizes and impregnated.

In contrast, it could be confirmed that when the silica colloid was not mixed (Comparative Example 1) in the synthesis step, Pd nanoparticles having a large size were impregnated in a small amount, but when the silica colloid was mixed, Pd nanoparticles having a small size were impregnated in a large amount.

Experimental Example 2

The surface characteristics of the catalysts prepared in Examples 4 to 7 were measured, and are shown in Table 2. In addition, each surface area of the catalysts was measured by an electron microscope, and is shown in FIGS. 7A to 10B.

TABLE 2

| Sample | | Heat treatment Temperature (° C.) | $A_{BET}$ (m²·g⁻¹) | $D_{BJH}$ (nm) | V (cm³·g⁻¹) | Metal loading/×10⁻¹ mmol/$g_{cat}$ | Average size of Pd (nm) |
|---|---|---|---|---|---|---|---|
| Example 4 | Pd/PDMC-900-16 | 900 | 934 | 9.2 | 2.2 | 1.3 | 1.6 |
| Example 5 | Pd/PDMC-800-16 | 800 | 1080 | 9.4 | 2.5 | 1.5 | 1.6 |
| Example 6 | Pd/PDMC-700-16 | 700 | 845 | 8.4 | 1.8 | 1.4 | 1.5 |
| Example 7 | Pd/PDMC-500-16 | 500 | 510 | 3.4 | 0.4 | 1.5 | 1.7 |

When FIGS. 7A to 10B were examined, it could be confirmed that as the heat treatment temperature was increased, the specific surface area of the catalyst was usually increased, but particularly, when the heat treatment temperature was 800° C., the specific surface are of the catalyst was most greatly increased.

Experimental Example 3

The dehydrogenation reaction of formate was performed by using the catalysts according to Examples 1 to 8 and Comparative Examples 1 and 2. Specifically, 5 mL of 1 M sodium formate and 25 mg of each of the catalysts prepared according to Examples 1 to 8 and Comparative Example 1 were reacted at 80° C. Further, in the case of the catalyst according to Comparative Example 2, 5.0 mg of the catalyst was reacted. Thereafter, the turnover frequency in each case was measured, and is shown in Table 3 and FIGS. 11A to 11D.

TABLE 3

| | Pd/PDMC-T-X | | |
|---|---|---|---|
| | T (Heat treatment temperature) | X (Content of silica colloid) | Turnover frequency (h⁻¹) |
| Comparative Example 1 | 1000 | 0 | No reaction |
| Example 1 | 1000 | 4 | 813 |
| Example 2 | 1000 | 8 | 1054 |
| Example 3 | 1000 | 16 | 1396 |
| Example 4 | 900 | 16 | 1570 |
| Example 5 | 800 | 16 | 1854 |
| Example 6 | 700 | 16 | 1515 |
| Example 7 | 500 | 16 | 1281 |
| Example 8 | 800 | 16 | 2562 |
| Comparative Example 2 | Pd/C | — | 1034 |

When Table 3 and FIGS. 11A to 11D were examined, it could be confirmed that the larger the amount of silica colloid was, the higher the surface area of the catalyst became, and accordingly, high catalytic activity values were exhibited. Meanwhile, it could be confirmed that when the heat treatment was performed at 800° C. (Examples 5 and 8) in the case of carbonization (heat treatment) temperature, the highest activity was exhibited, and it could be confirmed that particularly, these catalysts exhibited better catalytic activity than Pd/C catalysts most of which are commercially available.

Experimental Example 4

The hydrogenation reaction of bicarbonate was performed by using the catalysts according to Examples 3 to 8 and Comparative Example 2. Specifically, 10 mL of 1 M HCO₃Na and 50 mg of the catalyst were reacted under conditions of 80° C. and 40 bar for 24 hours. Thereafter, the conversion rate and turnover number thereof were measured and are shown in Table 4.

TABLE 4

| | Pd/PDMC-T-X | | | |
|---|---|---|---|---|
| | T (Heat treatment temperature) | X (Content of silica colloid) | Conversion rate (%) | Turnover number (TON) |
| Example 3 | 1000 | 16 | 70 | 770 |
| Example 4 | 900 | 16 | 73 | 985 |
| Example 5 | 800 | 16 | 82 | 1144 |
| Example 6 | 700 | 16 | 74 | 1018 |
| Example 7 | 500 | 16 | 22 | 311 |
| Example 8 | 800 | 16 | 65 | 1646 |
| Comparative Example 2 | Pd/C | — | 52 | 333 |

When Table 4 was examined, it could be confirmed that when the heat treatment was performed at 800° C. in the carbonization process, the catalyst exhibited the highest activity in the hydrogenation reaction of bicarbonate, and it could be confirmed that particularly, the catalyst prepared in the present Example exhibited better catalytic activity than Pd/C catalysts all of which are commercially available.

Experimental Example 5

Figure 12A:
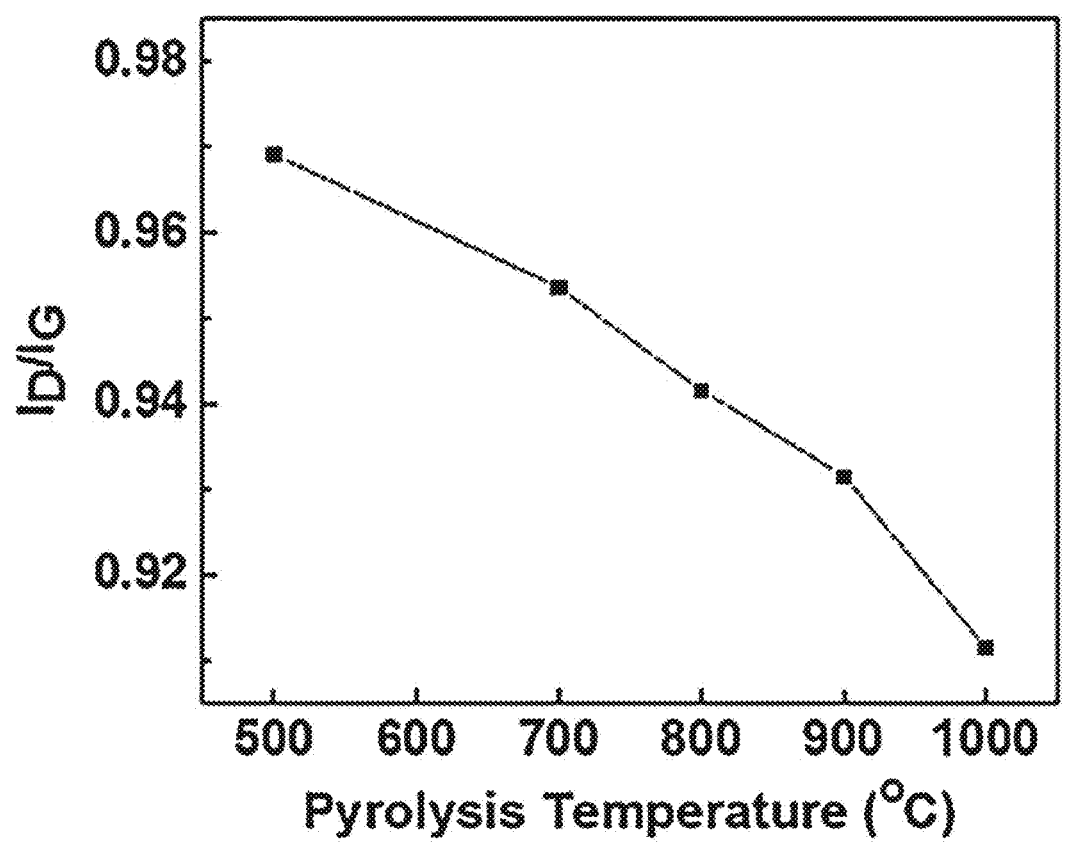
FIG. 12A is a graph showing the Raman analysis results of the catalysts prepared according to Examples.
Figure 12B:
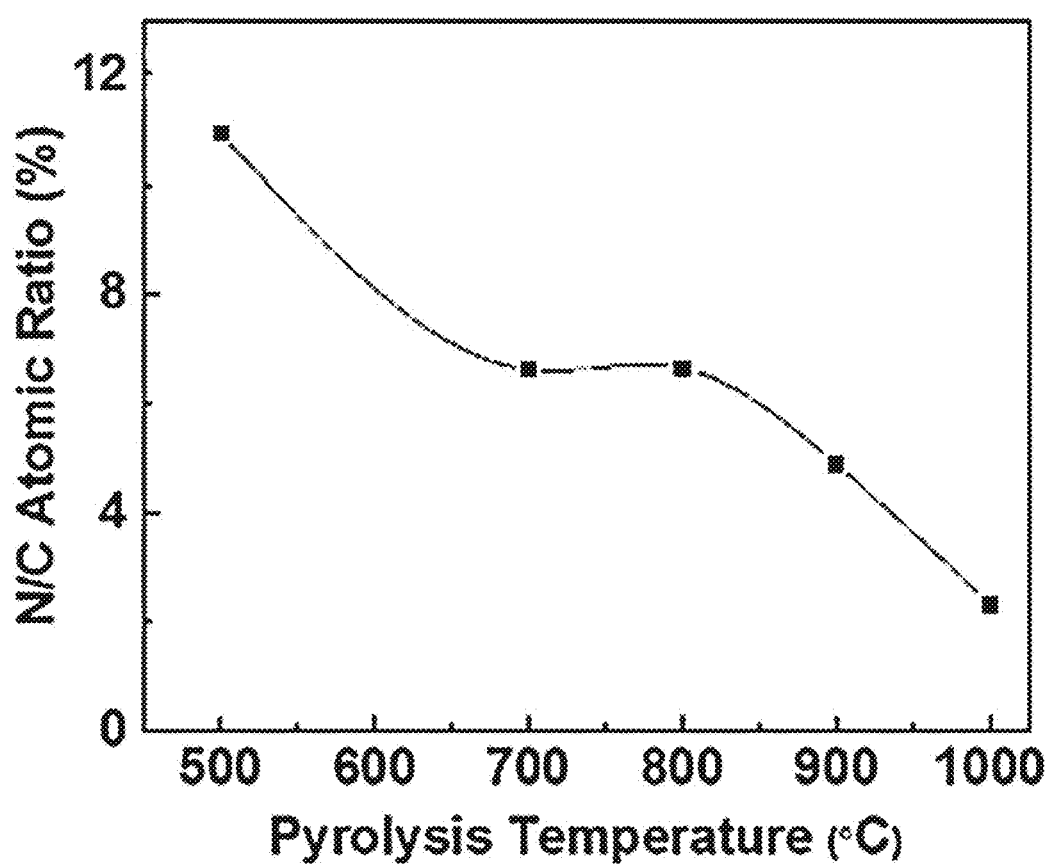
FIG. 12B is a graph showing an atomic ratio of nitrogen/carbon obtained from an XPS analysis result.

The catalysts prepared in Examples 3 to 7 were analyzed by using XPS (FIG. 12A), and the atomic ratios of nitrogen/hydrogen thereof were measured (FIG. 12B). Among them, the distribution forms of the catalysts according to Examples 3 to 7 were observed, and are shown in FIG. 12C.

As the carbonization temperature was increased, the amount of carbon carbonized was increased, and when the ratio of N/C in FIG. 12B was examined, it could be confirmed that when the carbonization temperature was 500° C., nitrogen was present in the largest amount, and as the temperature was increased, the ratio of N/C was lowered. That is, it could be confirmed that even though the ratio of nitrogen (N) was decreased and the carbonization temperature was decreased, the catalytic activity of the catalyst was excellent.

Figure 12C:
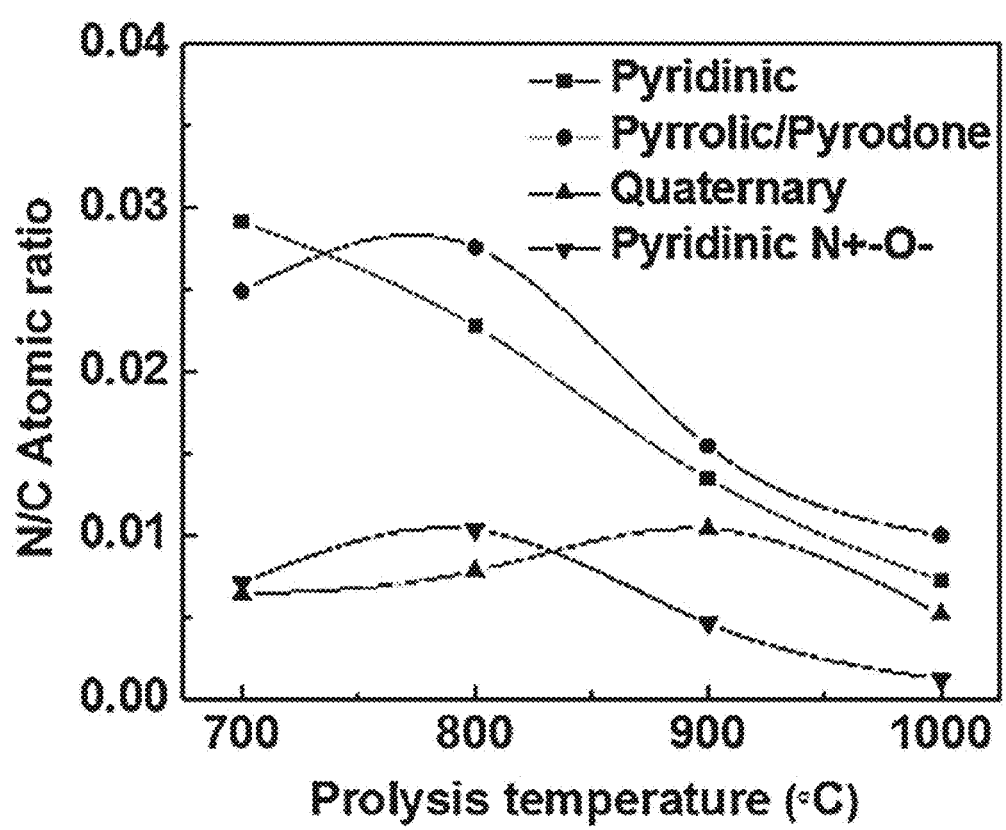
FIG. 12C is a graph showing a distribution form of a functional group including nitrogen obtained from the XPS analysis result.
Figure 12D:
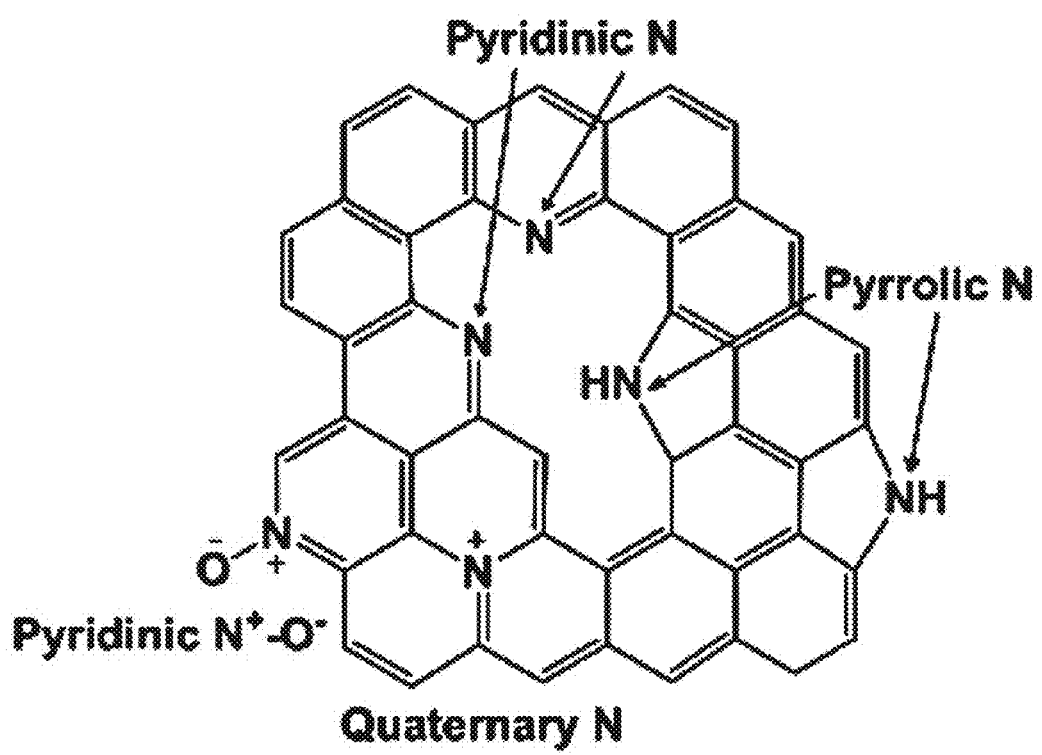
FIG. 12D is a schematic view showing a potential structure of an expected carbon support including a nitrogen atom.

Meanwhile, in the case of Example 5 in which the carbonization process was performed at 800° C. at which the catalytic activity is the best as in FIG. 12C, the pyrrolinized or pyridinized structure was exhibited most abundantly, and as a result, it could be known that the two structures positively affect the catalytic activity.

That is, when the support is doped with a heteroatom such as nitrogen, it is natural that catalytic activity is increased because nitrogen transports electrons to Pd to increase the electron density, but it could be confirmed that not only the amount of nitrogen, but also the electron density of Pd have been further increased because the case where the support is doped with a heteroatom becomes a state where electrons are transported to Pd more easily than the case where nitrogen is present in a structure of pyrroline or pyridine as in Example 5. That is, it could be confirmed that the amount of nitrogen was not only important, but it also affects the catalyst whether nitrogen is present in what form in the support.

Experimental Example 6

When the hydrogenation reaction of bicarbonate was performed by using the catalyst prepared in Example 3, gases to be discharged were detected, and components thereof were detected and are shown in Table 5.

TABLE 5

| | $H_2$ | $O_2$ | $N_2$ | $CH_4$ | CO | $CO_2$ |
|---|---|---|---|---|---|---|
| Content (%) | 38.7 | 7.4 | 48.1 | 0 | 0 | 0 |

When Table 5 was examined, it could be confirmed that when the hydrogenation reaction was performed by using the catalyst prepared according to the present disclosure, carbon monoxide (CO) was not generated. Accordingly, it could be confirmed that a gas harmful to the catalyst was not generated, and thus, the activity of the catalyst could be sustained.

The Examples of the present disclosure previously described should not be interpreted to limit the technical spirit of the present disclosure. The scope of the present disclosure to be protected is limited only by the matters described in the claims, and those skilled in the art of the present disclosure can improve and change the technical spirit of the present disclosure in various forms. Therefore, such improvements and changes would fall within the scope of the present disclosure to be protected as long as they are obvious to those skilled in the art.

What is claimed is:

1. A catalyst for a dehydrogenation reaction of formate and a hydrogenation reaction of bicarbonate, the catalyst comprising:
    a polyaniline-based porous carbon support, in which palladium particles are fixed,
    wherein the catalyst further comprises a region in which nitrogen is included, and
    wherein the catalyst has a specific surface area of 500 to 1,200 $(m^2 \cdot g^{-1})$.

2. The catalyst according to 9, wherein the polyaniline-based porous carbon support is a reaction product of a reaction of removing silica particles from a carbon composite produced via carbonization of a poly(silica-aniline) composite, and
    wherein the poly(silica-aniline) composite is a reaction product produced by mixing and reacting a silica colloid in a polymerization step of polyaniline.

3. The catalyst according to 9, wherein the catalyst has a spherical structure, and the region in which nitrogen is included has a pyridinized or pyrrolinized structure.

4. A method for releasing and storing hydrogen via a dehydrogenation reaction of formate and a hydrogenation reaction of bicarbonate using the catalyst according to claim 1.

* * * * *

UNITED STATES PATENT AND TRADEMARK OFFICE
CERTIFICATE OF CORRECTION

PATENT NO. : 10,688,474 B2
APPLICATION NO. : 15/719692
DATED : June 23, 2020
INVENTOR(S) : Chang Won Yoon et al.

It is certified that error appears in the above-identified patent and that said Letters Patent is hereby corrected as shown below:

In the Specification

Under the CROSS-REFERENCE TO RELATED APPLICATION and above BACKGROUND, add the following phrases:
This invention was made with government support under grant number DMR1508611 awarded by the National Science Foundation. The government has certain rights in the invention.

Signed and Sealed this
Fourth Day of March, 2025

Coke Morgan Stewart
*Acting Director of the United States Patent and Trademark Office*